(12) United States Patent
Roh et al.

(10) Patent No.: US 9,469,587 B2
(45) Date of Patent: Oct. 18, 2016

(54) STYRENATED PHENOL COMPOUND AND A METHOD OF PREPARING THE SAME

(71) Applicant: Korea Kumho Petrochemical Co., Ltd., Seoul (KR)

(72) Inventors: Kee Yoon Roh, Daejeon (KR); Jung Hee Jang, Daejeon (KR); Je Young Park, Busan (KR)

(73) Assignee: Korea Kumho Petrochemical Co., Ltd, Seoul (KR)

( * ) Notice: Subject to any disclaimer, the term of this patent is extended or adjusted under 35 U.S.C. 154(b) by 0 days.

(21) Appl. No.: 14/748,459

(22) Filed: Jun. 24, 2015

(65) Prior Publication Data

US 2015/0376098 A1    Dec. 31, 2015

(30) Foreign Application Priority Data

Jun. 27, 2014  (KR) .................. 10-2014-0080151

(51) Int. Cl.

| | | |
|---|---|---|
| *C07C 239/22* | (2006.01) | |
| *C07C 39/15* | (2006.01) | |
| *C09D 7/12* | (2006.01) | |
| *C07C 211/09* | (2006.01) | |
| *C07C 211/10* | (2006.01) | |
| *C07C 211/11* | (2006.01) | |
| *C07C 211/12* | (2006.01) | |
| *C08G 59/62* | (2006.01) | |

(52) U.S. Cl.

CPC ............ *C07C 39/15* (2013.01); *C07C 211/09* (2013.01); *C07C 211/10* (2013.01); *C07C 211/11* (2013.01); *C07C 211/12* (2013.01); *C08G 59/621* (2013.01); *C09D 7/1233* (2013.01)

(58) Field of Classification Search
None
See application file for complete search history.

(56) References Cited

FOREIGN PATENT DOCUMENTS

| | | |
|---|---|---|
| CN | 102267876 A | 12/2011 |
| CN | 102549041 A | 7/2012 |

OTHER PUBLICATIONS

Mamedova et al. (Petroleum Chemistry, 2007, 47(1), 55).*
Office Action dated Jan. 22, 2016 in Taiwanese Application No. 10520076560.

* cited by examiner

*Primary Examiner* — Sudhakar Katakam
*Assistant Examiner* — Jennifer C Sawyer
(74) *Attorney, Agent, or Firm* — Saliwanchik, Lloyd & Eisenschenk

(57) ABSTRACT

A styrenated phenol compound in which a hydrazine or a diaminoalkane compound binds to a styrenated phenol, and a method of preparing the same are provided. The styrenated phenol compound may have improved exterior quality and storage stability of a product by maintaining a hardening stimulation property and plasticity and preventing discoloration when mixed with a hardener for an epoxy paint.

16 Claims, 1 Drawing Sheet

STYRENATED PHENOL COMPOUND AND A METHOD OF PREPARING THE SAME

CROSS-REFERENCE TO RELATED APPLICATION

This application claims the benefit under 35 U.S.C. §119 of Korean Application No. 10-2014-0080151, filed Jun. 27, 2014, which is hereby incorporated by reference in its entirety.

BACKGROUND

1. Field of the Invention

The present invention relates to a styrenated phenol compound and a method of preparing the same, and more particularly, to a styrenated phenol compound in which a hydrazine or a diaminoalkane compound binds to a styrenated phenol and a method of preparing the same.

2. Discussion of Related Art

To provide plasticity to a conventional hardener composition of an epoxy paint and stimulate hardening, an alkyl phenol, particularly, a nonylphenol or styrenated phenol compound has been used.

The alkyl phenol has an anionic molecular structure in a molecule because a hydroxyl hydrogen atom of phenol is dehydrogenated due to basicity of a mixed hardener, and here, the generated anion has a quinone-type structure due to resonance in the molecule, and thus turns yellow or red.

A degree of discoloration is determined by a rate of transforming into the quinone-type according to a basicity level of the used hardener. When a tertiary amine hardener having strong basicity is used, the discoloration rapidly progresses, and when a primary amine hardener is used, the discoloration may be delayed somewhat, but may not be ultimately prevented.

Since the discoloration may degrade exterior quality and storage stability of a product, the necessity for a colorless hardener composition, which is not changed in color, is increasing, and particularly, a demand for a product to be applied to a transparent flooring material is greatly increasing.

However, a conventional alkyl phenol compounds (nonylphenol, dodecylphenol and octylphenol) is limitedly used due to chemical toxicity, and when mixed with a hardener, the styrenated phenol compound can be discolored.

To solve such a problem, the inventor developed a styrenated phenol compound which has improved exterior quality and storage stability of a product by maintaining plasticity and a hardening stimulation property and preventing the discoloration of a hardener composition, when mixed with the hardener.

SUMMARY OF THE INVENTION

The present invention is directed to a styrenated phenol compound which can have improved exterior quality and storage stability of a product by maintaining properties of a plasticizer composition, for example, a hardening stimulation property and plasticity, and preventing the discoloration of a hardener composition, when mixed with the hardener, and a method of preparing the same.

One aspect of the present invention provides a styrenated phenol compound represented by Formula 1 in which a hydrazine or a diaminoalkane compound binds to a styrenated phenol.

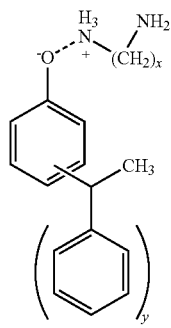

[Formula 1]

In Formula 1, x is one of the integers from 0 to 20, and y is one of the integers from 1 to 3.

In one embodiment, the styrenated phenol may include a monostyrenated phenol, a distyrenated phenol, and a tristyrenated phenol.

In one embodiment, a content of the monostyrenated phenol may be 50 wt % or more based on a total weight of the styrenated phenol.

In one embodiment, the diaminoalkane compound may be at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

In one embodiment, a content of the hydrazine or the diaminoalkane compound may be 0.1 to 10 wt % based on a total weight of the styrenated phenol compound.

Another aspect of the present invention provides a hardener composition for a paint, which includes a main component of a hardener; and a styrenated phenol compound represented by Formula 1 in which a hydrazine or a diaminoalkane compound binds to a styrenated phenol.

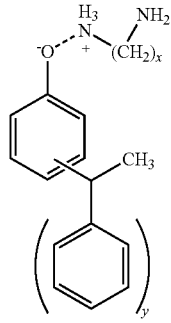

[Formula 1]

In Formula 1, x is one of the integers from 0 to 20, and y is one of the integers from 1 to 3.

In one embodiment, the styrenated phenol may include a monostyrenated phenol, a distyrenated phenol, and a tristyrenated phenol.

In one embodiment, a content of the monostyrenated phenol may be 50 wt % or more based on a total weight of the styrenated phenol.

In one embodiment, the diaminoalkane compound may be at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

In one embodiment, a content of the hydrazine or the diaminoalkane compound may be 0.1 to 10 wt % based on a total weight of the styrenated phenol compound.

In one embodiment, contents of the main component for the hardener and the styrenated phenol compound may be 70 to 90 wt % and 10 to 30 wt %, respectively, based on a total weight of the hardener composition.

Still another aspect of the present invention provides a method of preparing a styrenated phenol compound, which includes synthesizing a styrenated phenol by performing alkylation of a phenol and a styrene, and preparing a compound represented by Formula 1 by adding a hydrazine or a diaminoalkane compound to the styrenated phenol.

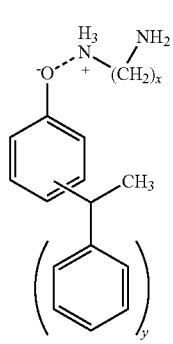

[Formula 1]

In Formula 1, x is one of the integers from 0 to 20, and y is one of the integers from 1 to 3.

In one embodiment, the styrenated phenol may include a monostyrenated phenol, a distyrenated phenol, and a tristyrenated phenol.

In one embodiment, a content of the monostyrenated phenol may be 50 wt % or more based on a total weight of the styrenated phenol.

In one embodiment, the diaminoalkane compound may be at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

In one embodiment, a content of the hydrazine or the diaminoalkane compound may be 0.1 to 10 wt % based on a total weight of the styrenated phenol compound.

The styrenated phenol compound in which the hydrazine or the diaminoalkane compound binds to the styrenated phenol can replace the conventional compound such as nonylphenol or dodecylphenol, and thus can have improved exterior quality and storage stability of a product by maintaining properties of the hardener such as a hardening stimulation property and plasticity and preventing the discoloration of a hardener composition, when mixed with the hardener, and have improved workability by reducing time to harden a paint.

The effect of the present invention is not limited to the above-described effects, but it should be understood that the present invention includes all of the effects which can be deduced from the configuration of the present invention described in the detailed description or claims of the present invention.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
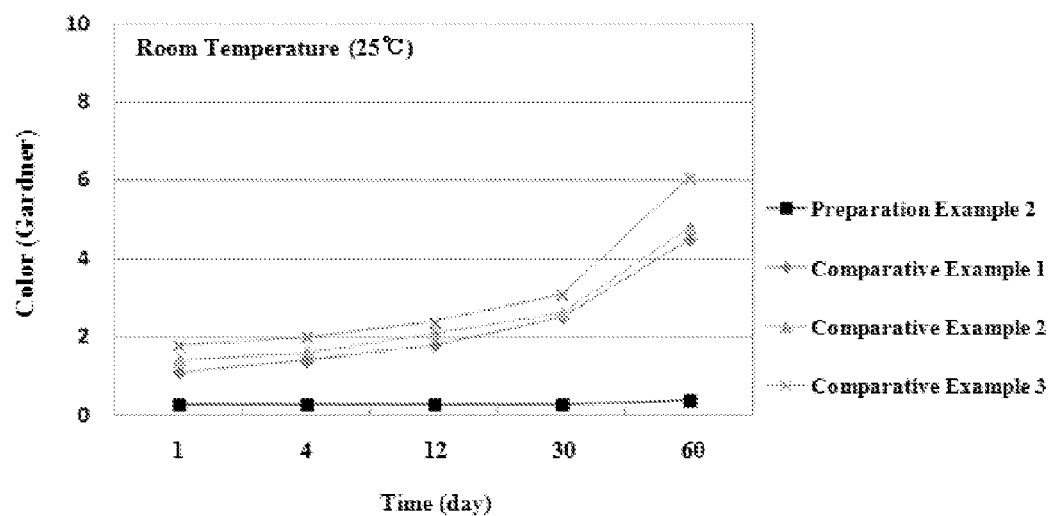
FIG. 1 is a graph showing the result of a room temperature (25° C.) discoloration test for a hardener composition including a styrenated phenol compound according to an exemplary embodiment of the present invention.

Exemplary embodiments of the present invention will be described in detail below with reference to the accompanying drawings. However, the present invention may be realized in various different forms, and therefore is not limited to examples to be described herein. In addition, to clearly explain the present invention, parts not relating to the descriptions will be omitted, and like reference marks denote the like parts throughout the specification.

In the specification, when one part "includes" a component, unless particularly described otherwise, it means that the part can further include a different component, not excluding the component.

Hereinafter, examples of the present invention will be described in detail with reference to the accompanying drawings.

Styrenated Phenol Compound

One aspect of the present invention provides a styrenated phenol compound represented by Formula 1 in which a hydrazine or a diaminoalkane compound binds to a styrenated phenol.

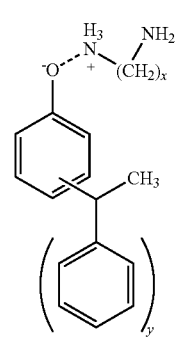

[Formula 1]

In Formula 1, x is one of the integers from 0 to 20, and y is one of the integers from 1 to 3.

The styrenated phenol may be a mixture including a monostyrenated phenol, a distyrenated phenol, and a tristyrenated phenol, and a content of the monostyrenated phenol may be 50 wt % or more based on a total weight of the mixture. When a structure of the styrenated phenol is a mixture of at least two styrenated phenols having different structures, a styrenated phenol compound produced therefrom may also be a mixture or composition consisting of at least two types of styrenated phenol compounds having different structures.

When phenol and styrene are alkylated at 100 to 150° C. in the presence of an acid catalyst, monostyrenated phenol (hereinafter, referred to as "MSP") in which one styrene binds to a benzene ring of the phenol, distyrenated phenol (hereinafter, referred to as "DSP") in which two styrenes bind to a benzene ring of the phenol and tristyrenated phenol (hereinafter, referred to as "TSP") in which three styrenes bind to a benzene ring of the phenol may be generated, and a ratio of each product may be determined according to an equivalent ratio of reactants, for example, the phenol and the styrene, a type of a catalyst or a reaction temperature.

In addition, a content of MSP of the generated styrenated phenol may be 50 wt % or more, and preferably, 50 to 80 wt %, based on a total weight of the styrenated phenol.

When the MSP content is 50 wt % or more, viscosity is reduced to provide plasticity when mixed with a hardener, and thus workability can be improved, and a hydroxyl value (OH value) may be maintained in a level similar to conventional nonylphenol (240 to 250) to stimulate hardening.

The hydrazine or the diaminoalkane compound may be added to the styrenated phenol, thereby forming a styrenated phenol compound, particularly, a styrenated phenol adduct, in which a nitrogen atom of the hydrazine or the diaminoalkane compound binds to a hydroxyl hydrogen atom of the styrenated phenol.

The hydrazine may be a liquid hydrazine, or a hydrazine hydrate ($N_2H_4 \cdot H_2O$) to which water is added. However, the hydrazine is a colorless water-absorbing liquid, and present in an ultimately unstable state in which heat is emitted in the air to induce a strong alkali reaction. Therefore, the hydrazine may be the hydrazine hydrate for stability.

In a hardener composition formed by mixing the styrenated phenol adduct with a hardener, instead of the hydroxyl hydrogen atom of the styrenated phenol, a hydrogen atom included in an amino group of the hydrazine or the diaminoalkane compound (C1 to C20) may be dehydrogenated, and thus a hydroxyl group of the styrenated phenol remains, thereby preventing discoloration of the hardener composition.

The diaminoalkane compound may be at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

A content of the hydrazine or the diaminoalkane compound may be 0.1 to 10 wt %, preferably, 0.1 to 5 wt %, and more preferably, 0.1 to 3 wt %, based on a total weight of the styrenated phenol compound.

When the content of the hydrazine or the diaminoalkane compound is less than 0.1 wt %, it is difficult to obtain a property of preventing required discoloration, and when the content of the hydrazine or the diaminoalkane compound is more than 10 wt %, reaction efficiency and storage stability may be degraded due to a remaining hydrazine or diaminoalkane compound that does not bind to the styrenated phenol.

Hardener Composition Including Styrenated Phenol Compound

Another aspect of the present invention provides a hardener composition for a paint including a main component of a hardener, and a styrenated phenol compound represented by Formula 1 in which a hydrazine or a diaminoalkane compound binds to a styrenated phenol.

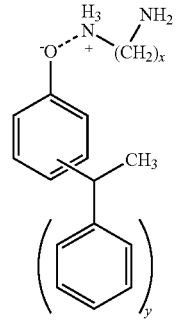

[Formula 1]

In Formula 1, x is one of the integers from 0 to 20, and y is one of the integers from 1 to 3.

The styrenated phenol may be a mixture including a monostyrenated phenol, a distyrenated phenol, and a tristyrenated phenol, and a content of the monostyrenated phenol may be 50 wt % or more, and preferably, 50 to 80 wt %, based on a total weight of the mixture. When the styrenated phenol is a mixture consisting of at least two types of styrenated phenols having different structures, a styrenated phenol compound produced therefrom may also be a mixture or composition consisting of at least two styrenated phenol compounds having different structures.

The diaminoalkane compound may be at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

A content of the hydrazine or the diaminoalkane compound may be 0.1 to 10 wt %, preferably, 0.1 to 5 wt %, and more preferably, 0.1 to 3 wt %, based on a total weight of the styrenated phenol compound.

The content of the hydrazine or the diaminoalkane compound and the effect realized thereby are the same as described above.

A content of the main component of the hardener and the styrenated phenol compound may be 70 to 90 wt % and 10 to 30 wt % based on a total weight of the hardener composition, respectively.

When the content of the styrenated phenol compound is less than 10 wt % based on a total weight of the hardener composition, it is difficult to provide plasticity or miscibility greater than that required to the main component of a hardener, and when the content of the styrenated phenol compound is more than 30 wt %, flowability of the paint excessively increases and thus exterior quality and storage stability of a paint-coated product may be degraded.

Method of Preparing Styrenated Phenol Compound

Still another aspect of the present invention provides a method of preparing a styrenated phenol compound, which includes: synthesizing a styrenated phenol by performing alkylation of a phenol and a styrene, and preparing a compound represented by Formula 1 by adding a hydrazine or a diaminoalkane compound to the styrenated phenol.

[Formula 1]

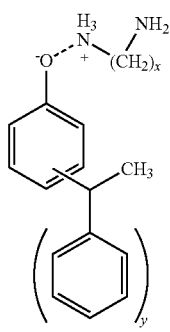

In Formula 1, x is one of the integers from 0 to 20, and y is one of the integers from 1 to 3.

In the synthesis of the styrenated phenol, the styrenated phenol may be synthesized by performing alkylation of the phenol and the styrene in the presence of a phosphoric acid catalyst and adding a sulfuric acid or a magnesium sulfate as a catalyst to terminate the alkylation.

As an initial reaction catalyst for synthesizing the styrenated phenol, the phosphoric acid ($H_3PO_4$) catalyst may be used. The phosphoric acid catalyst generally has a larger molecular size and a lower activity than the sulfuric acid catalyst, and thus a relatively high reaction temperature.

However, the phosphoric acid catalyst has lower reaction activity, but has higher selectivity than the sulfuric acid catalyst, and thus may change a composition ratio of the synthesized styrenated phenol. Particularly, a content of MSP in which one styrene is substituted may be 50 wt % or more, and preferably 60 wt % or more, based on a total weight of the synthesized styrenated phenol.

In addition, compared to the sulfuric acid catalyst, the phosphoric acid catalyst can substitute the styrene at a higher rate at a para site, which is the fourth site of the phenol, in the MSP, and thus product selectivity may be improved.

Meanwhile, when the alkylation is performed only with the phosphoric acid catalyst, unreacted phenols and styrenes may remain during the termination of the reaction. To remove the remaining unreacted materials, the sulfuric acid or the magnesium sulfate ($MgSO_4$) catalyst may be used during the termination of the reaction, which is the time or the period of the termination of the addition of the styrene as a reactant, so as to minimize an amount of the remaining unreacted materials.

An amount of the sulfuric acid or the magnesium sulfate catalyst used in the process may be 2 to 10 wt % based on a weight of the phosphoric acid catalyst, when the amount of the sulfuric acid or the magnesium sulfate catalyst is less than 2 wt %, a remnant removing effect may be insignificant, and when the amount of the sulfuric acid or the magnesium sulfate catalyst is more than 10 wt %, separation or recovery of the product is difficult.

After the alkylation, at least one aqueous solution selected from a group consisting of sodium carbonate ($Na_2CO_3$), potassium carbonate ($K_2CO_3$), sodium hydroxide (NaOH), potassium hydroxide (KOH) and a mixture thereof may be added to neutralize the alkylation product, and a produced neutralized salt may be removed using a filtration filter, thereby recovering the styrenated phenol.

Meanwhile, in the preparation of the styrenated phenol compound, specifically, a styrenated phenol adduct, by adding a hydrazine or a diaminoalkane compound, a nitrogen atom of the added hydrazine or diaminoalkane compound may provide an electron pair to a hydroxyl hydrogen atom of the styrenated phenol and thus the nitrogen atom and the hydroxyl hydrogen atom bind to each other.

The styrenated phenol may be a mixture including a monostyrenated phenol, a distyrenated phenol, and a tristyrenated phenol, and a content of the monostyrenated phenol may be 50 wt % or more, and preferably, 50 to 80 wt %, based on a total weight of the mixture. When the styrenated phenol is a mixture consisting of at least two styrenated phenols having different structures, the styrenated phenol compound produced therefrom may also be a mixture or composition consisting of at least two styrenated phenol compounds having different structures.

The diaminoalkane compound may be at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diamindodecane, diaminotridecane, diaminotetradecane, diaminopentadecane, diaminohexadecane, diaminoheptadecane, diaminoocatadecane, diaminononadecane, diaminoieicosane, and a hydrate thereof.

A content of the hydrazine or the diaminoalkane compound may be 0.1 to 10 wt %, preferably, 0.1 to 5 wt %, and more preferably 0.1 to 3 wt % based on a total weight of the styrenated phenol compound.

The content of the hydrazine or the diaminoalkane compound and the effect realized thereby are the same as described above.

Hereinafter, examples of the present invention will be described in detail.

Examples 1 to 4

Preparation of Styrenated Phenol Compound 300 g of phenol and 2.0 g of a phosphoric acid ($H_3PO_4$) catalyst were put into a reaction vessel, and heated to 140° C., and 380.0 g of styrene was dropped for 120 minutes. As the styrene was dropped, a reaction temperature was elevated to 170° C. After the dropping of the styrene, the resulting product was further reacted at the same reaction temperature for one hour.

To remove unreacted remnants, the reaction temperature was lowered to 110° C., and 0.02 g of a sulfuric acid ($H_2SO_4$) catalyst was added to the reactant. As the sulfuric acid catalyst was added, the reaction temperature was elevated again to 125° C., and the reaction was further performed in this state for 30 minutes. The temperature of the reactants was lowered to 80° C., and then the reactants were neutralized for 30 minutes by adding a sodium carbonate aqueous solution at the same equivalent ratio as the sulfuric acid. The neutralized salt produced thereby was subjected to vacuum evaporation to remove water and filtered, thereby obtaining styrenated phenol (reaction conversion rate: 97%, purity: 97% or more).

As the obtained styrenated phenol was analyzed through gas chromatography (GC), it was confirmed that MSP, DSP and TSP were produced at ratios of 67 wt %, 27 wt % and 6 wt %, respectively.

Hydrazine hydrate ($N_2H_4 \cdot H_2O$) was added and bound to the obtained styrenated phenol at 0.1 to 10 wt % based on a total weight of a styrenated phenol compound, thereby preparing a styrenated phenol compound represented by Formula 2.

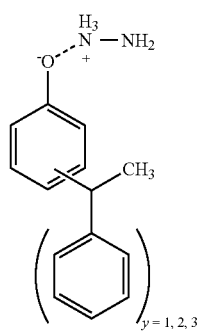

[Formula 2]

The components used to prepare the styrenated phenol compounds of Examples 1 to 4 and the contents thereof are shown in Table 1.

TABLE 1

| Division | Styrenated phenol | Hydrazine hydrate |
|---|---|---|
| Example 1 | 99.9 | 0.1 |
| Example 2 | 99.0 | 1.0 |
| Example 3 | 95.0 | 5.0 |
| Example 4 | 90.0 | 10.0 |

(Unit: wt %)

Preparation Examples 1 to 4

Hardener Composition Including Styrenated Phenol Compound

Hardener compositions for an epoxy paint of Preparation Examples 1 to 4 were prepared by mixing each of the styrenated phenol compounds according to Examples 1 to 4 with known hardeners for an epoxy paint, i.e., Jeffamine 230, isophorone diamine (IPDA) and 2,4,6-Tris[(dimethylamino)methyl]phenol, K-54 (DMP-30) at a predetermined composition ratio through stirring using a magnetic stirrer for 30 minutes.

Meanwhile, the hardener compositions of Comparative Examples 1 to 3 were prepared by mixing nonylphenol, dodecylphenol and octylphenol, respectively, with the same hardener for an epoxy paint through stirring. Variables required to prepare other hardener compositions were controlled in the same manner as described in Preparation Examples 1 to 4.

Compositions of the hardener compositions according to Preparation Examples 1 to 4 and Comparative Examples 1 to 3 are shown in Table 2.

TABLE 2

| | Epoxy hardener | | | Plasticizer | | | | | | |
|---|---|---|---|---|---|---|---|---|---|---|
| Division | Jeffamine D230 | IPDA | DMP-30 (K-54) | Example 1 | Example 2 | Example 3 | Example 4 | Nonyl phenol | Dodecyl phenol | Octyl phenol |
| Preparation Example 1 | 25 | 50 | 10 | 15 | — | — | — | — | — | — |
| Preparation Example 2 | | | | — | 15 | — | — | — | — | — |
| Preparation Example 3 | | | | — | — | 15 | — | — | — | — |
| Preparation Example 4 | | | | — | — | — | 15 | — | — | — |
| Comparative Example 1 | | | | — | — | — | — | 15 | — | — |
| Comparative Example 2 | | | | — | — | — | — | — | 15 | — |
| Comparative Example 3 | | | | — | — | — | — | — | — | 15 |

(Unit: wt %)

Experimental Example 1

Discoloration Test at Room Temperature (25° C.)

To check discoloration at room temperature (25° C.) over time, the hardener compositions of Preparation Example 2 and Comparative Examples 1 to 3 were stirred at room temperature for 10 minutes, and the discolorations according to the passage of time at room temperature were measured using an OME-2000 color meter.

Experimental Example 2

Discoloration Test at High Temperature (60° C.)

Discoloration at a high temperature, compared to room temperature, is a critical factor having an influence on storage stability of the hardener composition. Thus, to confirm the discoloration according to time at high temperature (60° C.), the hardener compositions of Preparation Example 2 and Comparative Examples 1 to 3 were stirred at room temperature for 10 minutes, and the discoloration according to time at high temperature was measured using an OME-2000 color meter.

Figure 2:
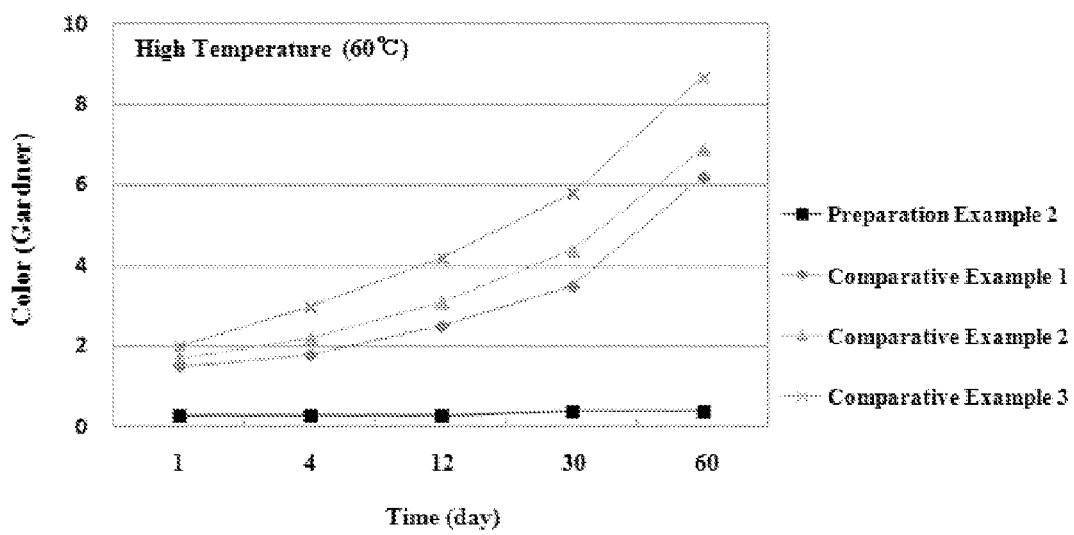
FIG. 2 is a graph showing the result of a high temperature (60° C.) discoloration test for a hardener composition including a styrenated phenol compound according to an exemplary embodiment of the present invention.

The results of the discoloration test according to Experimental Examples 1 and 2 are shown in Table 3, and FIGS. 1 and 2.

TABLE 3

| Division | Discoloration test at room temperature (25° C.) | | | | | Discoloration test at high temperature (60° C.) | | | | |
|---|---|---|---|---|---|---|---|---|---|---|
| | 1 day | 4 day | 12 day | 30 day | 60 day | 1 day | 4 day | 12 day | 30 day | 60 day |
| Preparation Example 2 | 0.3 | 0.3 | 0.3 | 0.3 | 0.4 | 0.3 | 0.3 | 0.3 | 0.4 | 0.4 |
| Comparative Example 1 | 1.1 | 1.4 | 1.8 | 2.5 | 4.5 | 1.5 | 1.8 | 2.5 | 3.5 | 6.2 |
| Comparative Example 2 | 1.4 | 1.6 | 2.1 | 2.6 | 4.8 | 1.7 | 2.2 | 3.1 | 4.4 | 6.9 |
| Comparative Example 3 | 1.8 | 2.0 | 2.4 | 3.1 | 6.1 | 2.0 | 3.0 | 4.2 | 5.8 | 8.7 |

Referring to Table 3, according to the result of the discoloration test at room temperature (25° C.) of Experimental Example 1, it is shown that, when one component of the hardener composition, a styrenated phenol compound prepared by adding and binding a hydrazine hydrate, was added as a plasticizer, compared to the hardener compositions of Comparative Examples 1 to 3 to which a conventional plasticizer component (nonylphenol, dodecylphenol or octylphenol) was added, the hardener composition of Preparation Example 2 had an improved effect of preventing discoloration and thus had excellent storage stability.

In addition, comparing the result of the discoloration test at room temperature (25° C.) and the result of the discoloration test at high temperature (60° C.), it is shown that the hardener composition of Preparation Example 2 had a considerably small discoloration range with respect to temperature deviation compared to those of Comparative Examples 1 to 3.

According to Experimental Examples 1 and 2, it was confirmed that the styrenated phenol compound to which the hydrazine hydrate was added and bound had more improved exterior quality of a product coated with a paint containing the hardener composition than the conventional plasticizer compound, due to an excellent effect of preventing discoloration of the hardener composition and excellent storage stability.

Experimental Example 3

Test for Measuring Hardening Rate of Paint

A target material was coated with 100 g of a paint mixture prepared by mixing each of 40 parts by weight of the hardener compositions of Preparation Example 2 and Comparative Examples 1 to 3 with respect to 100 parts by weight of an epoxy paint in which an epoxy resin (828, 218, or 331 grade) and benzyl alcohol (solvent) was mixed at a weight ratio of 90:10 and hardened at 25° C., and then time required for hardening was measured, and thus the result is shown in Table 4.

TABLE 4

| Epoxy paint | | | |
|---|---|---|---|
| Epoxy resin | Solvent | Hardener composition | Hardening time |
| KER-828 | Benzyl alcohol | Preparation Example 2 | 3 hrs 10 min |
| | | Comparative Example 1 | 3 hrs 28 min |
| | | Comparative Example 2 | 3 hrs 35 min |
| | | Comparative Example 3 | 3 hrs 50 min |

Referring to Table 4, it was confirmed that the hardening time of the epoxy paint composition in which the hardener composition of Preparation Example 2 was mixed was reduced to maximally 40 minutes compared to the paints in which the hardener compositions of Comparative Examples 1 to 3 was mixed. That is, according to Experimental Example 3, it is confirmed that the styrenated phenol compound to which the hydrazine hydrate was added and bound has a direct or indirect influence on the hardening rate of the epoxy paint composition, and particularly, compared to the conventional plasticizer compound, the styrenated phenol compound has a considerably high hardening rate of the epoxy paint composition.

The above descriptions of the present invention are provided as examples, and it will be apparent to those skilled in the art that various modifications can be easily made to the above-described exemplary embodiments of the present invention without departing from the spirit or scope of the invention. Thus, it should be understood that the exemplary embodiments described above are merely examples, but not limited. For example, the components explained in a single type can be realized separately, and components to be explained as separated may be realized as components binding to each other.

The scope of the present invention is represented by the following claims, and it should be construed that all modifications or modified forms deduced from the meaning and scope, and an equivalent concept of the claims are included in the scope of the present invention.

What is claimed is:

1. A styrenated phenol compound having the structure of Formula 1, in which a hydrazine or a diaminoalkane compound binds to a styrenated phenol:

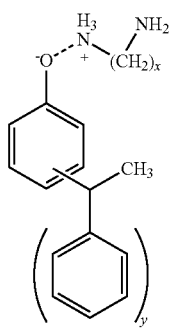

[Formula 1]

wherein x is one of the integers from 0 to 20, and y is one of the integers from 1 to 3.

2. The compound of claim 1, wherein the styrenated phenol includes a monostyrenated phenol, a distyrenated phenol, and a tristyrenated phenol.

3. The compound of claim 2, wherein a content of the monostyrenated phenol is 50 wt % or more based on a total weight of the styrenated phenol.

4. The compound of claim 1, wherein the diaminoalkane compound is at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

5. The compound of claim 1, wherein a content of the hydrazine or the diaminoalkane compound may be 0.1 to 10 wt % or more based on a total weight of the styrenated phenol compound.

6. A hardener composition for a paint, comprising:
a main component of a hardener; and
a styrenated phenol compound having the structure of Formula 1, in which a hydrazine or a diaminoalkane compound binds to a styrenated phenol:

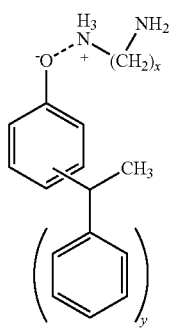

[Formula 1]

wherein x is one of the integers from 0 to 20, and y is one of the integers from 1 to 3.

7. The composition of claim 6, wherein the styrenated phenol includes a monostyrenated phenol, a distyrenated phenol, and a tristyrenated phenol.

8. The composition of claim 7, wherein a content of the monostyrenated phenol is 50 wt % or more based on a total weight of the styrenated phenol.

9. The composition of claim 6, wherein the diaminoalkane compound is at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

10. The composition of claim 6, wherein a content of the hydrazine or the diaminoalkane compound is 0.1 to 10 wt % based on a total weight of the styrenated phenol compound.

11. The composition of claim 6, wherein contents of the main component of the hardener and the styrenated phenol compound are 70 to 90 wt % and 10 to 30 wt %, respectively, based on a total weight of the hardener composition.

12. A method of preparing a styrenated phenol compound, comprising:
synthesizing a styrenated phenol by performing alkylation of a phenol and a styrene; and
preparing a compound represented by Formula 1 by adding a hydrazine or a diaminoalkane compound to the styrenated phenol,

[Formula 1]

wherein x is one of the integers from 0 to 20, and y is one of the integers from 1 to 3.

13. The method of claim 12, wherein the styrenated phenol includes a monostyrenated phenol, a distyrenated phenol, and a tristyrenated phenol.

14. The method of claim 13, wherein a content of the monostyrenated phenol is 50 wt % or more based on a total weight of the styrenated phenol.

15. The method of claim 12, wherein the diaminoalkane compound is at least one selected from the group consisting of diaminomethane, diaminoethane, diaminopropane, diaminobutane, diaminopentane, diaminohexane, diaminoheptane, diaminooctane, diaminononane, diaminodecane, diaminoundecane, diaminododecane, diaminotridecane, diaminotetradecane, diaminopentadecane, diaminohexadecane, diaminoheptadecane, diaminoocatadecane, diaminononadecane, diaminoieicosane, and a hydrate thereof.

16. The method of claim 12, wherein a content of the hydrazine or the diaminoalkane compound is 0.1 to 10 wt % based on a total weight of the styrenated phenol compound.

* * * * *